United States Patent [19]

Cohen et al.

[11] 4,019,255
[45] Apr. 26, 1977

[54] DENTAL APPARATUS FOR CHEEK RETRACTION AND SALIVA COLLECTION

[76] Inventors: Morton Cohen, Suite 604, Fox Pavilion, Jenkintown, Pa. 19046; Elliott Silverman, 4829 Atlantic Ave., Ventnor, N.J. 08406

[22] Filed: Oct. 16, 1975

[21] Appl. No.: 623,103

[52] U.S. Cl. .................................... 32/33; 128/12
[51] Int. Cl.² ........................................ A61C 17/04
[58] Field of Search ........ 32/33, 34, 35, 36, 37–39; 128/299, 300, 12

[56] References Cited

UNITED STATES PATENTS

| | | | |
|---|---|---|---|
| 2,859,519 | 11/1958 | Cohn | 32/33 |
| 3,027,643 | 4/1962 | Cohen | 32/33 |
| 3,241,550 | 3/1966 | Gelarie | 128/12 |
| 3,916,880 | 11/1975 | Schroer | 128/12 |

Primary Examiner—Robert Peshock
Attorney, Agent, or Firm—Robert K. Youtie

[57] ABSTRACT

A dental apparatus including a pair of cheek retractor elements for engaging respective opposite sides of a patient's mouth and yieldably urged apart to maintain cheeks retracted and afford mounting means for a saliva collector.

14 Claims, 3 Drawing Figures

DENTAL APPARATUS FOR CHEEK RETRACTION AND SALIVA COLLECTION

BACKGROUND OF THE INVENTION

While cheek retractors have been known and used in the past, such prior art devices have usually required handholding of individual retractor pieces, or involved relatively complex, cumbersome, unreliable and inconveniently located holding apparatus. Also, saliva collectors have heretofore been deficient in being incapable of specific optimal location, as overlying a saliva duct, being inefficient in operation so as to leave saliva pools and moisture on surfaces, and being generally uncomfortable to the patient and inconvenient to the dentist.

SUMMARY OF THE INVENTION

Accordingly, it is an important object of the present invention to provide a cheek retractor apparatus which overcomes the above mentioned difficulties, being quickly, easily and confortably inserted into the patient's mouth to effectively retract both cheeks at the same time while being self-holding in position without the need for manual holding or complex holding mechanisms.

It is a further object of the present invention to provide a cheek retractor of the type described which is extremely simple in construction, light in weight, and entirely reliable in operation throughout a long useful life.

A further object of the present invention resides in the provision of mounting means for a saliva collector, which mounting means may be a cheek retractor, whereby saliva receiver elements are selectively locatable to achieve maximum operating efficiency, as over a saliva duct, for effectively minimizing the presence of saliva and moisture in a patient's mouth.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described and of which the scope will be indicated by the appended claims.

BRIEF DESCRIPTIO OF THE DRAWINGS

DESCRIPTION OF THE PREFERRED EMBODIMENT

As is well known to those versed in the dental arts, cheek retraction is desirable in many operations, including dental photography, the filling of cavities, orthondontia, and particularly for all work requiring greater access into the mouth, say to second molars.

Also well known to those versed in the art is the desiderata of saliva collection and removal in many dental procedures. The collection and removal of saliva has become increasingly critical in the increasing use of adhesives, as in orthodontic practices, and also in the setting time of fillings.

Accordingly, the present invention is concerned both with cheek retraction and saliva collection, the dental apparatus disclosed herein serving to combine and greatly enhance the effectiveness of these functions.

Figure 1:
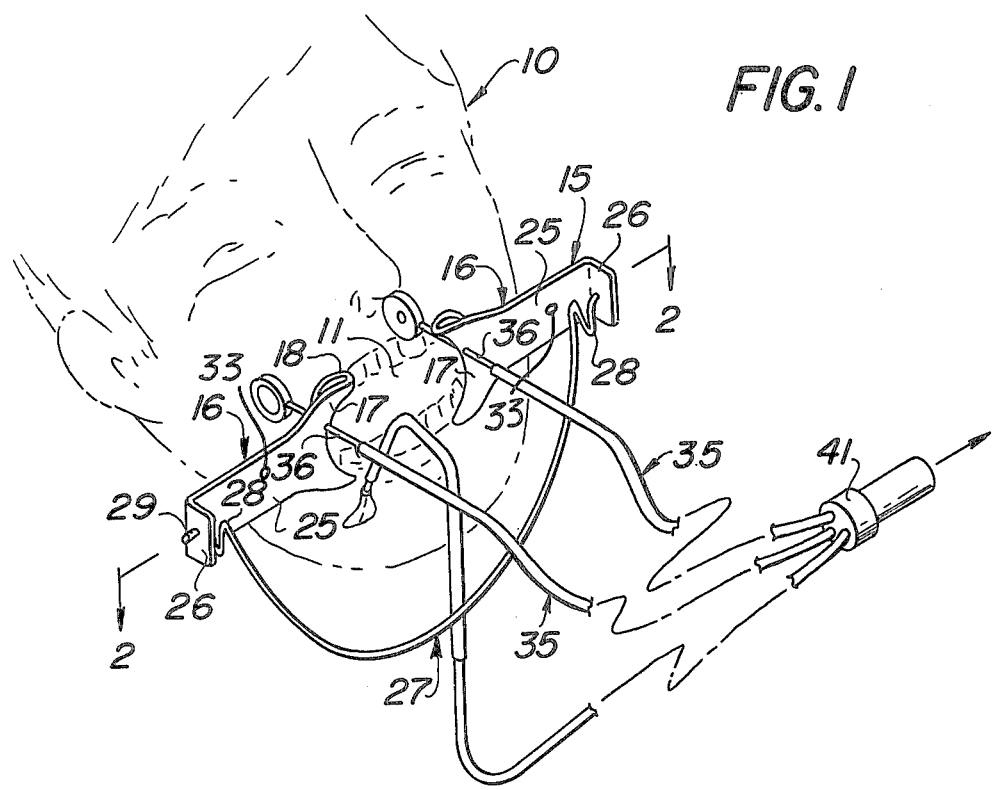
FIG. 1 is a top perspective view showing a dental apparatus of the present invention in operative association with a patient's mouth.

Referring now more particularly to the drawings, and specifically to FIG. 1 thereof, a patient is shown in phantom and generally designated 10. It will be seen that the patient's mouth 11 is open, the cheeks being retracted to expose the patient's teeth. In operative association with the patient's mouth is the dental apparatus of the present invention, generally designated 15.

In particular, the apparatus 15 includes a pair of separate cheek retractor elements 16, which may be substantially identical. Each retractor element 16 may include on its inner end a hook part 17 which may have a transversely extending channel-like portion 18 of U-shaped cross section. The channel-like hook part is arcuate or bowed so as to have its bight region externally concave.

More specifically, each channel-like hook part 17 includes an arcuate bight region 20 and opposite side walls 21 and 22 extending from the bight region. The bight region 20 is of a compound curvature, being arcuately concave in planes normal to the side walls 21 and 22 and facing into the space between the latter, and being arcuately convex in planes parallel to the side walls and facing into the space between the latter.

Thus, the hook parts 17 are configured for hooked engagement in opposite respective sides of a patient's mouth 11, the side walls 21 of each hook part engaging interiorly of the mouth or lips, as seen in FIG. 1. A generally straight extension or shank 25 may extend from the hooked part outer side wall 22, outwardly away from the mouth. The outer end of each shank 25 may terminate in a transverse or forwardly projecting lug 26. The lugs 26 provide connector means for connecting respective retractor elements 16 to opposite ends of a resiliently contractile element 27. In particular, the resiliently contractile element 27 may be a resilient wire having end formations 28 of lateral or transverse extent so as to define enlargements, and provided with terminal or end projections 29. Each end projection engages slidably and removably through a respective retractor element lug 26, each of the latter being provided with a through hole 30 for removably receiving a respective terminal projection 29.

Figure 3:
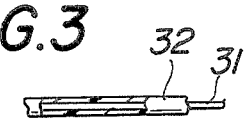
FIG. 3 is a fragmentary section, somewhat enlarged, of the area designated 3 in FIG. 2.

The resiliently contractile element may be defined by a stiff resilient wire, as at 31 in FIG. 3, preferably coated or sheathed, as at 32, say by rubber or plastic. For ease of insertion and withdrawal, the sheathing or plastic 32 may be removed from the terminal projections 29. Further, the enlargements 28 may be defined by undulant, transversely extending curvature, say of generally sine wave formation. The enlargements 28 therefore limit insertion through apertures 30 of lugs 26 to the terminal projections 29, and the element 27 is suitably contractile, say by resilient bending, as illustrated, to yieldably and resiliently urge the retractor elements 16 away from each other. This automatically retains the retractor elements 16 in cheek retracting position as the retractor hook parts 17 are hooked about opposite respective sides of the patient's mouth. A degree of adjustment of the resilient force applied by contractile element 27 through retractor elements 16 to the patient's mouth may be achieved by deformation of undulant curves 28 to increase or decrease the overall dimension thereof. The cheek retractor shanks 25 are each advantageously provided, medially of its ends, with a through opening or aperture 33. The ends of resiliently bendable and contractile element 27 are selectively engageable, respectively, through one or both of openings 33 to apply a desired retractng force to the cheeks. For example, relatively large force may be applied by inserting both terminal projections 29 through respective openings 33, and an intermediate amount of force may be applied by inserting one projection 29 through one opening 33 of one retractor element and the other projection 29 through the opening 30 of the other retractor element. Thus, the projections 29 may combine with selected openings or holes 30 and 33 for connection of the contractile element 27 to the elongate or shank parts 25 of the retractor elements 16.

In addition to the cheek retractor device described hereinbefore, the dental apparatus 15 includes saliva collector means 35 which may be associated with each retractor element 16 and mounted thereby in a selected position for maximum saliva removal.

Figure 2:
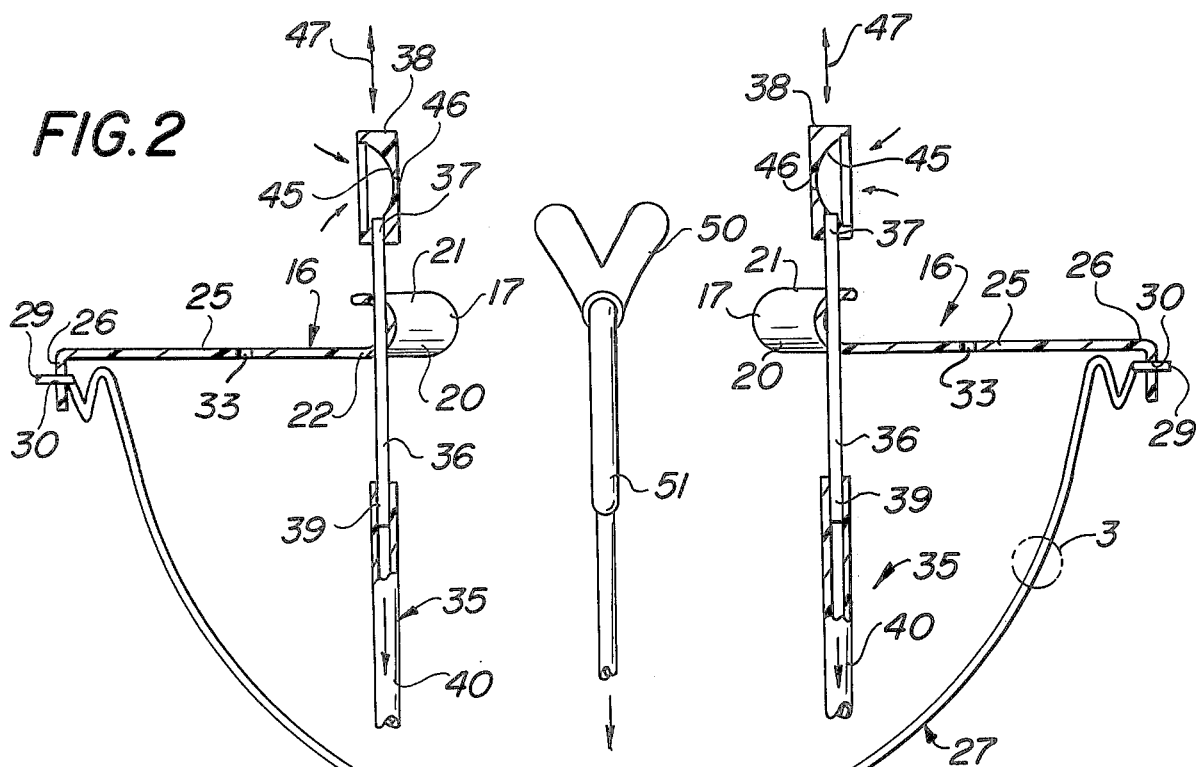
FIG. 2 is a generally horizontal sectional view taken approximately along the line 2—2 of FIG. 1 showing the dental apparatus apart from the patient's mouth.

More specifically, each saliva collector 35 includes a conduit or tube 36 extending slidably through a respective retractor element 16. As in the illustrated embodiment, a tube 36 may extend slidably through the associated hook part 17, passing through and generally normal to the pair of hook part walls 21 and 22, best seen in FIG. 2. The tube 36 may be relatively stiff and suitably selectively positionable along its path of sliding movement relative to the associated cheek retractor 16. One end of conduit or tube 36 enters the patient's mouth 11, the interior tube end being designated 37 and carrying a saliva receiver 38. The other, exterior end 39 or tube 36 is provided with flexible conduit or hose 40 for communication, as by connector 41 to a source of vacuum or suction.

Each receiver 38 may be concave or hollow on one side, as at 45, and may be generally round or disc-shaped, as illustrated, or other suitable configuration for conforming engagement with the interior of a patient's mouth overlying a saliva duct. A small suction release or vent hole 46 may be provided centrally of receiver cup 38 of a size sufficient to reduce the suction force applied to the mouth tissue to avoid injury.

In practice, the saliva collectors 35 are arranged with their saliva-receiving cups 38 over respective saliva ducts to effect direct removal of saliva from the mouth, rather than from a pool of saliva formed in the mouth. The accurate location of receiver cups 38 is facilitated by selective longitudinal sliding adjustment of tubes 36, as indicated by arrows 47. Also, conduits or tubes 36 may be of a bendable, form-retaining character, if desired.

The saliva collector system may include an additional saliva receiver 50 suitably configured for engagement over the central saliva duct beneath the tongue, and provided with suction conduit means 51 for fluid communication with connector 41, so that substantially all saliva is directly removed from the mouth without a chance to vaporize or in any way interfere with the dental procedure being carried on.

It will now be appreciated that the cheek retractor structure may be utilized without the saliva collector structure as a complete system. Further, the cheek retractor structure may be employed in conjunction with the saliva collection structure to both perform their intended functions in cooperation with each other, and also, the cheek retractor structure may serve as a mounting structure for the saliva collector system even when cheek retraction is not required. Hence, the retraction and collection structures combine with each other and enhance each other's effectiveness.

While it has been found practical to fabricate certain parts of plastic, such as the retractor elements 16, and other parts of metal, such as the resiliently contractile element 27, it is appreciated that other suitable materials may be employed, as desired.

Also, it is appreciated that the specific configurations of saliva receiver cups 38 and 50 may be of different sizes and shapes, as desired, say for accommodation to different mouth shapes and sizes, greater or lesser saliva capacity and suction-holding power, or for other reasons.

From the foregoing, it is seen that the present invention provides a combination cheek retractor and saliva collector for dental use which is extremely simple and lightweight in construction, durable and reliable in operation, is easy and convenient in use both by the patient and operator, and which otherwise fully accomplishes its intended objects.

Although the present invention has been described in some detail by way of illustration and example for purposes of clarity of understanding, it is understood that certain changes and modifications may be made within the spirit of the invention.

What is claimed is:

1. In a dental apparatus, a pair of cheek retractor elements each comprising a hook part for engaging a patient's lips at a respective side of the mouth, a shank part extending from each hook part outwardly away from each other and the patient's mouth entirely exteriorly thereof, connector means on an outer region of each shank part remote from the patient's mouth, and a resiliently contractile element extending between and connected to said connector means for yieldably urging the latter apart, said contractile element being generally curved in use to extend in spaced relation exteriorly about the patient's mouth and present no obstacle to the dental operator.

2. A dental apparatus according to claim 1, said contractile element comprising an elongate stiff resilient element.

3. A dental apparatus according to claim 2, said connector means comprising outstanding lugs, and said stiff resilient element including end formations engageable with said lugs.

4. An orthodontic apparatus according to claim 3, said elongate stiff resilient element comprising spring wire, and said end formations each comprising a terminal projection and an adjacent transversely enlarged portion, said terminal projections each being engageable into a respective lug as limited by the adjacent transversely enlarged portion.

5. A dental apparatus according to claim 4, said transversely enlarged portions each comprising an undulant configuration adapted to be longitudinally deformed to adjust the resilient contractile force.

6. A dental apparatus according to claim 1, said connector means comprising receiver openings, and said stiff resilient element including end formations interengageble with said receiver openings.

7. A dental apparatus according to claim 1, in combination with a saliva collector tube carried by each cheek retractor element having an exterior end for connection to a suction source and an interior end extending into the patient's mouth on a respective mouth side, and a saliva receiver on the interior end of each collector tube.

8. A dental apparatus according to claim 7, said receiver each comprising a cup for location over a respective saliva duct.

9. A dental apparatus according to claim 8, said collector tubes being longitudinally adjustably carried by said retractor elements for location of said receivers over said ducts.

10. A dental apparatus comprising a pair of hook parts for engaging a patient's lips at respective sides of the mouth, a shank part extending from each hook part outwardly away from each other and the patient's mouth, connector means on an outer region of each shank part, a resiliently contractile element extending between and connected to said connector means for yieldably urging the latter apart, a saliva collector tube carried by each retractor element having an exterior end for connection to a suction source and an interior end extending into the patient's mouth on a respective mouth side, and a saliva receiver on the interior end of each collector tube, said receiver each comprising a cup for location over a respective saliva duct, said saliva collector cups each having a vent opening to ameliorate forces applied to the mouth tissues.

11. In a dental apparatus, the combination comprising a mounting structure for location on a patient's face without obstructing access to the teeth, a pair of saliva collector tubes carried by said mounting structure each having an exterior end for connection to a suction force and having its inteior end extending into the patient's mouth on the respective mouth side, and a saliva receiver on the interior end of each collector tube, said mounting structure comprising a pair of hook parts for engaging a patient's lips at respective opposite sides of the mouth, a shank part extending from each hook part outwardly away from each other and the patient's mouth entirely exteriorly thereof, connector means on an outer region of each shank part remote from the patient's mouth, and a resiliently contractile element extending between and connected to said connector means for yieldably urging the latter apart, said contractile element being generally curved in use to extend in spaced relation about the patient's mouth and present no obstacle to the dental operator, said collector tubes each extending through a respective hook part for mounting thereby.

12. The combination according to claim 11, said receivers each comprising a cup for location over a respective saliva duct.

13. The combination according to claim 12, said collector tubes being longitudinally adjustably carried by said mounting structure for location of said receivers over said ducts.

14. In a dental apparatus, the combination comprising a mounting structure for location on a patient's face without obstructing access to the teeth, a pair of saliva collector tubes carried by said mounting structure each having an exterior end for connection to a suction force and having its interior end extending into the patient's mouth on the respective mouth side, and a saliva receiver on the interior end of each collector tube, said receivers each comprising a cup for location over a respective saliva duct, said saliva collector cups each having a vent opening for ameliorating forces applied to the mouth tissues.

* * * * *